United States Patent [19]
Shen et al.

[11] Patent Number: 5,345,020
[45] Date of Patent: Sep. 6, 1994

[54] METHOD FOR MAKING DIAMONDOID LUBRICANT BASE STOCK BY ALKYLATION WITH AN OLEFIN IN THE PRESENCE OF A LEWIS ACID

[75] Inventors: Dong-Ming Shen, Langhorne, Pa.; Margaret M. Wu, Skillman, N.J.

[73] Assignee: Mobil Oil Corporation, Fairfax, Va.

[21] Appl. No.: 70,823

[22] Filed: Jun. 3, 1993

[51] Int. Cl.$^5$ ............................................. C07C 13/28
[52] U.S. Cl. ..................................... 585/352; 585/375
[58] Field of Search ................................. 585/352, 375

[56] References Cited

U.S. PATENT DOCUMENTS

| | | | |
|---|---|---|---|
| 3,382,288 | 5/1968 | Schneider | 585/352 |
| 3,457,318 | 7/1969 | Capaldi et al. | 260/666 |
| 3,560,578 | 2/1971 | Schneider | 260/648 |
| 3,580,964 | 5/1971 | Driscoll | 260/871 |
| 3,639,362 | 2/1972 | Duling et al. | 260/78.5 |
| 3,649,702 | 3/1972 | Pincock et al. | 260/666 M |
| 3,676,521 | 7/1972 | Stearns et al. | 260/683.1 |
| 3,737,477 | 6/1973 | Stearns et al. | 260/683.15 D |
| 3,748,359 | 7/1973 | Thompson | 260/563 P |
| 3,832,332 | 8/1974 | Thompson | 260/78 R |
| 3,851,011 | 11/1974 | Stearns et al. | 260/683.15 D |
| 3,903,301 | 9/1975 | Share | 424/321 |
| 3,923,919 | 12/1975 | Stearns et al. | 260/683.1 |
| 3,928,480 | 12/1975 | Tabushi et al. | 585/352 |
| 3,966,624 | 6/1976 | Duling et al. | 252/52 R |
| 3,972,243 | 8/1976 | Driscoll et al. | 74/200 |
| 3,976,665 | 8/1976 | Feinstein et al. | 260/346.3 |
| 4,043,927 | 8/1977 | Duling et al. | 252/52 R |
| 4,082,723 | 4/1978 | Mayer et al. | 260/45.8 N |
| 4,142,036 | 2/1979 | Feinstein et al. | 528/183 |
| 4,168,260 | 9/1979 | Wiezer et al. | 260/45.8 NT |
| 4,182,922 | 1/1980 | Schick et al. | 585/18 |
| 4,239,927 | 12/1980 | Brennan et al. | 585/24 |
| 4,332,964 | 6/1982 | Bellmann et al. | 560/141 |
| 4,463,201 | 7/1984 | Schick et al. | 585/10 |
| 4,520,221 | 5/1985 | Hsia Chen | 585/517 |
| 4,547,613 | 10/1985 | Garwood et al. | 585/533 |
| 4,912,272 | 3/1990 | Wu | 585/10 |
| 5,043,503 | 8/1991 | Del Rossi et al. | 585/360 |
| 5,053,568 | 10/1991 | Chen | 585/21 |

FOREIGN PATENT DOCUMENTS

| | | | |
|---|---|---|---|
| 0089355 | of 0000 | Japan | 585/352 |
| 2012152 | 7/1975 | Japan | 585/352 |
| 654598 | 10/1976 | U.S.S.R. | 585/352 |

*Primary Examiner*—Asok Pal
*Attorney, Agent, or Firm*—Alexander J. McKillop; Dennis P. Santini; Robert B. Furr, Jr.

[57] ABSTRACT

The invention provides a method for selectively alkylating a diamondoid compound comprising reacting at least one α-olefin containing at least six carbon atoms with at least one diamondoid compound in the presence of an acid catalyst selected from the group consisting of $AlX_3$ and $BX_3$ wherein X is a halogen, in the absence of added proton-donating catalyst promoter. The invention further provides a lubricant composition comprising alkyl-substituted adamantanes wherein the ratio of linear to branched alkyl substituents is at least about 4:1 and wherein the average number of alkyl substitutions per diamondoid molecule is from about 1.5 to about 4.

11 Claims, No Drawings

METHOD FOR MAKING DIAMONDOID LUBRICANT BASE STOCK BY ALKYLATION WITH AN OLEFIN IN THE PRESENCE OF A LEWIS ACID

CROSS-REFERENCE TO RELATED APPLICATIONS

This application is related by disclosure of similar subject matter to application Ser. No. 08/070,815, pending.

FIELD OF THE INVENTION

The present invention relates generally to the field of high performance synthetic lubricants. More particularly, the invention relates to lubricant compositions and methods for synthesizing thermally and oxidatively stable lubricant compositions which exhibit high viscosity for a given molecular weight.

BACKGROUND OF THE INVENTION

Adamantane has been found to be a useful building block in the synthesis of a broad range of organic compounds. For a general survey of the chemistry of adamantane and the its higher homologs including diamantane and triamantane, see *Adamantane, The Chemistry of Diamond Molecules*, Raymond C. Fort, Marcel Dekker, New York, 1976. The following references provide a general overview of adamantane polymer chemistry.

U.S. Pat. No. 3,457,318 to Capaldi et al. teaches the preparations of polymers of alkenyl adamantanes and alkenyl adamantanes useful as coatings, electrical appliance housings, and transformer insulation. The process, yielding polymers bonded through the tetrahedral bridgehead carbons, comprises contacting an adamantyl halide in the presence of a suitable catalyst with a material selected from the group consisting of substituted allyl halides and olefins to produce adamantyl dihaloalkanes or adamantyl haloalkanes as an intermediate product. The intermediate product is then dehalogenated or dehydrohalogenated, respectively, to produce the alkenyl adamantane final product.

U.S. Pat. No. 3,560,578 to Schneider teaches the reaction of adamantane or alkyladamantanes with a $C_3$–$C_4$ alkyl chloride or bromide using $AlCl_3$ or $AlBr_3$ as the catalyst. The reference describes polymerization through $C_3$–$C_4$ linkages connecting bridgehead carbon atoms in the starting adamantane hydrocarbon; See column 3, lines 35–55, as well as the structural illustrations in columns 3–5.

U.S. Pat. No. 3,580,964 to Driscoll discloses polyesters containing hydrocarbyladamantane moieties as well as novel intermediate diesters and crosslinked polymers prepared therefrom. The hydrocarbyladamantane moieties are bonded through the tetrahedral bridgehead carbons; See column 2, lines 6–46 and the diesters illustrated in column 3, lines 55–75.

U.S. Pat. No. 3,639,362 to Dulling et al. discloses novel copolymers having low mold shrinkage properties which are prepared from adamantane acrylate and methacrylates. The adamantane molecule is bonded to the polymer chain through tetrahedral bridgehead carbon atoms.

U.S. Pat. No. 3,649,702 to Pincock et al. discloses a reactive derivative of adamantane, 1,3-dehydroadamantane. The reference shows bridgehead substituents including halogens and alkyls; See column 1, lines 45–64.

U.S. Pat. No. 3,748,359 to Thompson teaches the preparation of an alkyladamantane diamine from an alkyladamantane diacid. The diamine product is illustrated at column 1, lines 20–30, clearly showing bonding through the bridgehead carbons.

U.S. Pat. No. 3,832,332 to Thompson teaches a polyamide polymer prepared from an alkyladamantane diamine. As discussed and illustrated in the Thompson '332 patent at column 2, lines 41–53, the polymer comprises repeating units which include the backbone structure of adamantane. Note that the adamantane structure is bonded to the polymer chain through its bridgehead carbons.

U.S. Pat. No. 3,903,301 to Gates et al. teaches a limited-slip differential lubricant composition which may optionally include adamantane. See in particular the list of $C_{13}$–$C_{29}$ naphthenes at column 4, line 1 et seq.

U.S. Pat. No. 3,966,624 to Duling et al. teaches a power transmission fluid containing a saturated adamantane compound. The adamantane compound consists of adamantane-like structures connected through ester linkages, ether linkages, carboxylic acids, hydroxyl or carbonyl groups; See the Abstract as well as column 1, line 49 through column 2, line 50.

U.S. Pat. No. 3,976,665 to Feinstein et al. discloses a dianhydride containing an adamantane group bonded through the bridgehead carbons.

U.S. Pat. No. 4,043,927 to Duling et al. teaches a tractive drive which may optionally contain an alkyladamantane or alkyladamantanol dimer of the $C_{12}$–$C_{19}$ range containing from 1 to 3 alkyl groups of the $C_1$–$C_3$ range, wherein the dimer contains two adamantane nuclei which are linked together through an alkylene radical derived from and having the same number of carbon atoms as an alkyl group of the starting adamantane material.

U.S. Pat. No. 4,082,723 to Mayer et al. discloses aza-adamantane compounds for stabilizing polymers to retard degradation by light and heat. The compounds have an adamantane backbone structure with at least one bridgehead carbon replaced by nitrogen. Specified bridgehead carbons may also be replaced by phosphorus, a phosphoryl or thiophosphoryl group, or a methine group optionally substituted by a phenyl or methyl group; See column 1, line 4 through column 2, line 16.

U.S. Pat. No. 4,142,036 to Feinstein et al. discloses adamantane compounds having 2 to 4 bridgehead positions substituted with phenylacyl moieties suitable for producing polymers useful for forming shaped objects such as film, fiber, and molded parts. The ester-substituted adamantanes are also suitable as plasticizers for polyvinylchloride and other polymers. The Feinstein et al. '036 patent notes that the four bridgehead carbons are equivalent to each other and are also more susceptible to attack than the secondary carbons.

U.S. Pat. No. 4,168,260 to Weizer et al. teaches nitrogen-substituted triaza-adamantanyl ureas useful as stabilizers for thermoplastic materials. Nitrogen replaces carbon in three of the four bridgehead positions.

U.S. Pat. No. 4,332,964 to Bellmann et al. discloses diacrylate and dimethacrylate esters containing bridgehead substituted adamantane monomers. The polymer synthesis technique disclosed at column 3, line 62 through column 7, line 61 includes halogen addition at bridgehead carbons followed by replacement of the halogen with the selected link of the polymer chain.

The following references are representative of the art of lubricant-grade synthetic oligomers.

U.S. Pat. Nos. 3,676,521, 3,737,477, 3,851,011, and 3,923,919 to Stearns et al. teach lubricants having high Viscosity Index, low pour point, and high stability which comprise ethylene-propylene copolymers produced from monoolefin mixtures containing ethylene and propylene over catalysts including vanadium-aluminum or titanium-aluminum Ziegler-type catalyst systems.

U.S. Pat. No. 3,972,243 to Driscoll et al. discloses compositions including traction fluids, antiwear additives, as well as lubricant stocks containing a gem-structured hydrocarbon backbone, which compositions are produced by ozonolysis of polyolefins, particularly polyisobutylene oligomers.

U.S. Pat. No. 4,182,922 to Schick et al. teaches a synthetic hydrocarbon oil and a method of making the same involving the copolymerization of propylene plus higher 1-olefins with small amounts of ethylene.

U.S. Pat. No. 4,239,927 to Brennan et al. relates to a process for producing synthetic hydrocarbon oils by the pooymerization of olefins using an aluminum halide catalyst. More specifically, the reference provides a method for preventing accumulation of certain organic halides which were found to be corrosive to process equipment by reacting such organic halides with aromatic hydrocarbons to evolve an alkylation product.

U.S. Pat. No. 4,463,201 to Schick et al. discloses a process for producing high quality synthetic lubricating oils by the copolymerization of ethylene, propylene, and a third 1-olefin, and subsequently dewaxed via a urea adduction process.

U.S. Pat. No. 4,520,221 to Chen teaches a process for producing high Viscosity Index lubricants from light olefins over a catalyst having the structure of ZSM-5, the surface acidity of which has been inactivated by treatment with a suitable base material.

U.S. Pat. No. 4,547,613 to Garwood et al. teaches the conversion of olefin-rich hydrocarbon streams such as ethylene and containing up to about 16 carbon atoms to high Viscosity Index lubricant base stocks by contacting the olefins with a catalyst having the structure of ZSM-5 under elevated pressure.

U.S. Pat. No. 4,912,272 to Wu relates to lubricant mixtures having unexpectedly high viscosity indices. More specifically, the lubricant mixtures comprise blends of high Viscosity Index polyalphaolefins prepared with activated chromium on silica, polyalphaolefins prepared with $BF_3$, aluminum chloride, or Ziegler-type catalysts.

The preceding references elucidate several advantageous aspects of synthetic lubricant, including high Viscosity Index, as well as good lubricity and thermal stability. Thus it would be highly desirable to provide a relatively low molecular weight high viscosity synthetic lubricant blending stock for increasing the kinematic viscosity of blended synthetic lubricants.

U.S. Pat. No. 5,043,503 to Del Rossi et al. teaches a process for alkylating polycycloparaffinic compounds (such as diamondoids) in the presence of zeolite catalysts to produce a lubricant stock.

U.S. Pat. No. 5,053,568 to Chen et al. teaches a lubricant additive and composition comprising the copolymer of 1-vinyladamantane and a 1-alkene.

SUMMARY OF THE INVENTION

This invention provides a lubricant composition with high thermal and oxidative stability. The invention further provides a method for selectively alkylating a diamondoid compound having at least one unsubstituted bridgehead hydrogen with at least one $C_6+\alpha$-olefin in the presence of an acidic catalyst selected from the group consisting of $AlX_3$ and $BX_3$ wherein X is a halogen, and in the absence of an added active proton-containing additive. The term "active proton-containing additive" as used herein refers to active proton-containing compounds such as water, alcohols, and HX, wherein X is a halogen, which compounds can readily release a proton.

The method of this invention selectively alkylates diamondoid compounds while avoiding substantial self-polymerization of the $\alpha$-olefin alkylating agent.

DETAILED DESCRIPTION

Feedstocks

Diamondoid compounds having at least one bridgehead hydrogen (i.e., at least one unsubstituted bridgehead position) are useful feedstocks in the present invention. The diamondoid feed may comprise a single diamondoid compound, or a mixture of diamondoid compounds.

The ratio of $\alpha$-olefinic alkylating agent to the diamondoid compound ranges from about 20:1 to less than about 1:1, preferably from about 6:1 to about 1:1.

The alkyl-substituted diamondoid compounds are useful feedstocks with the limitation that the diamondoid backbone structure must contain at least one readily alkylatable reaction site. Further, the substituent groups surrounding the alkylatable reaction site or sites must be sufficiently small to avoid hindering the alkylation agent's access to the reaction site or sites.

Recovery of diamondoid compounds, one such class of polycyclic alkanes, from natural gas is detailed in U.S. Pat. Nos. 4,952,748, 4,952,749, 4,982,049, 4,952,747, 5,016,712, 5,126,274, 5,139,621 and 5,120,899, which patents are incorporated herein by reference for details of the recovery methods.

Generally the alkyl groups which can be present as substituents on the diamondoid compounds in the feedstock contain from 1 to about 30 carbon atoms and preferably from about 1 to 10 carbon atoms, and most preferably from about 1 to 5 carbon atoms.

Other suitable polycyclic alkane feedstocks include diamondoids such as adamantane, diamantane, and triamantane, as well as tricyclo[5.2.1.0]decane, bicyclo[2.2.2]octane, bicyclopentayl, bicyclohexyl, decahydronaphthalene, dicyclohexylmethane, perhydrofluorene, perhydroanthracene, dicyclohexylcyclohexane, and dicyclopentylcyclopentane. Higher molecular weight alkylhydroaromatic hydrocarbons can also be used as starting materials and include polycycloparaffinic hydrocarbons such as are produced by the alkylation of polycyclic paraffins with olefin oligomers. Examples of such products include butyl-tetralin, decyl-indan, dodecyl-fluorene, and dodecyl-anthracene.

The $\alpha$-Olefin Alkylating Agents

The alkylating agents which are useful in the process of this invention generally include the $\alpha$-olefins which contain at least six carbon atoms. The method of this invention selectively alkylates the diamondoid feed with the $\alpha$-olefin or mixture of $\alpha$-olefins. The $\alpha$-olefins useful as alkylating agents may contain up to 40 or more carbon atoms, and $\alpha$-olefins having from about 8 to about 20 carbon atoms are preferred. Examples of suitable $\alpha$-olefins include 1-octene, 1-nonene, 1-decene, 1-undecene, 1-dodecene, 1-tridecene, 1-tetradecene, 1-pentadecene, 1-hexadecene, 1-heptadecene, and 1-octadecene. Alkylating agents such as 1-decanol, 1-tetradecanal, 1-hexadecanol, 1,4-butanadiol, 1,8-octanediol; and, alkyl halides such as 1-chlorobutane, 1-chlorooctane, 1-chlorotetradecane, 1-bromodecane, and 1-bromohexadecane, are also useful for adding alkyl groups to diamondoid compounds, in the presence of the catalyst of this invention.

Mixtures of alpha-olefins are especially useful as alkylating agents in the alkylation process of this invention. Accordingly, mixtures of 1-octene, 1-nonene, 1-decene, 1-undecene, 1-dodecene, 1-tridecene, 1-tetradecene, 1-pentadecene, 1-hexadecene, 1-heptadecene, and 1-octadecene, are most preferred. For example, a typical mixed alpha-olefin stream preferred for use in the present process possesses the following composition:

| Alpha Olefin | Weight Percent |
|---|---|
| $C_6$ | 7 |
| $C_8$ | 10 |
| $C_{10}$ | 15 |
| $C_{12}$ | 13 |
| $C_{14}$ | 14 |
| $C_{16}$ | 9 |
| $C_{18}$ | 7 |
| $C_{20}+$ | 25 |

Catalysts

Catalysts useful for producing the lubricant of the present invention include metals as well as solid and liquid acidic catalysts, which are conventionally used for Friedel-Crafts reactions. The catalyst of this invention must contain no added compounds which would tend to readily release protons. Examples of such compounds which should be excluded from the reaction mixture include water, alcohols, and ethers, and HX wherein X is a halogen. Useful liquid acidic catalysts are exemplified by $BF_3$ complexes, as well as by a solution or complex of an aluminum halide, such as the chloride or bromide, which may be neat or which may be dissolved in a suitable solvent such as hexanes. The aluminum halide may be dissolved in a halogenated organic solvent, for example, a methylene halide such as methylene chloride or methylene bromide. For a discussion of liquid aluminum halide catalysts in synthetic lubricant synthesis from olefins, see U.S. Pat. Nos. 4,239,927 to Brennan et al., cited above, and incorporated by reference as if set forth at length herein.

Conversion Conditions

Process conditions useful for synthesizing the lubricant additives of the present invention are shown below in Table 1.

TABLE 1

| | Conversion Conditions | |
|---|---|---|
| | Broad Range | Preferred Range |
| Temperature, °C. | −40–200 | 0–80 |
| Pressure, psig | 0–1000 | 0–50 |
| Contact Time, hrs. | 0.25–100 | 4–16 |

TABLE 1-continued

| | Conversion Conditions | |
|---|---|---|
| | Broad Range | Preferred Range |
| Molar Olefin-to-Diamondoid Ratio | 20:1–1:1 | 6:1–1:1 |

The diamondoid feedstock of the invention may be produced by mixing individual diamondoid components, by blending mixtures of diamondoids, or by fractionating and treating a naturally occurring diamondoid mixture. U.S. Pat. No. 5,120,899 to Chen and Wentzek teaches a particularly preferred method for recovering a diamondoid-containing mixture from a natural gas stream, and is incorporated by reference as if set forth at length herein.

The lubricant base stock of this invention comprises alkyl-substituted diamondoids having a ratio of linear to branched alkyl substituents of at least about 4:1 and an average number of alkyl substitutions per diamondoid molecule of from about 1.5 to about 6. The lubricant base stock of the invention may be used neat or may be blended with a synthetic or petroleum-based lubricant stock. Examples of useful synthetic lubricant blending stocks are taught in U.S. Pat. No. 4,943,383 to Avery et al., U.S. Pat. No. 4,952,303 to Bortz et al., U.S. Pat. No. 4,962,249 to Chen et al., U.S. Pat. No. 4,967,029 to Wu, U.S. Pat. No. 4,967,032 to Ho et al., U.S. Pat. No. 4,990,709 to Wu, U.S. Pat. No. 4,990,718 to Pelrine, U.S. Pat. No. 4,990,238 to Cruzman et al., U.S. Pat. No. 4,992,189 to Chen et al., U.S. Pat. No. 4,995,962 to Degnan, Jr., et al., U.S. Pat. No. 5,012,020 to Jackson et al., U.S. Pat. No. 5,015,795 to Pelrine, U.S. Pat. No. 5,068,046 to Blain et al., and U.S. Pat. No. 5,095,165 to Hsia Chen. These patents are incorporated herein for teaching synthetic lubricant blending components.

EXAMPLES

Examples 1–5 demonstrate the reaction of adamantane and alpha-olefin using $AlBr_3/CH_2Br_2$ catalyst. The general procedure for Examples 1–5 follows.

To a suspension of adamantane and n-hexane in a roundbottom flask fitted with a reflux condenser having a nitrogen bubbler and a pressure-equalized addition funnel were added 1.0M $AlBr_3$ in $CH_2Br_2$, and then an alpha-olefin was added dropwise from the funnel to the flask with stir at about 0° C.~room temperature. After stirring for an additional period after finishing addition of the olefin, the mixture was poured into ice-water. The layers were separated and the aqueous layer washed with hexanes. The combined organic layers were washed with water and saturated sodium chloride. After drying with anhydrous $Na_2SO_4$, the solvent was removed. The crude product was further purified with Kugelrohr and/or distillation. Table 1 lists specific conditions for these runs. Table 2 compares the properties of the total alkylate products. The VI of the products increased with the chain length of the alpha-olefins used. Surprisingly, the pour points did not deteriorate in the range of alpha-olefins examined in these examples. The products showed much better thermal stability than regular PAO type products exemplified by Examples 6 and 7.

TABLE 1

Reaction conditions for alkylation of adamantane with alpha-olefins using AlBr$_3$/CH$_2$Br$_2$

| Example Number | Ad—H g | alpha-Olefin used compound | g | mmol AlBr$_3$ | n-hexane mL | Reaction T° C. | Reaction time, hrs adding olefin | after adding |
| --- | --- | --- | --- | --- | --- | --- | --- | --- |
| 1 | 13.62 | 1-hexene | 50.50 | 5.0 | 75 | ~70 | 0* | 36 |
| 2 | 6.81 | 1-hexene | 42.08 | 1.0 | 25 | r.t. to ~40 | 2 | 4 |
| 3 | 27.25 | 1-octene | 79.25 | 4.0 | 100 | ~r.t. | 5.2 | 15 |
| 4 | 13.62 | 1-decene | 35.07 | 1.0 | 40 | 0 to r.t. | 0.25 | 5.25 |
| 5 | 13.62 | 1-decene | 70.14 | 1.0 | 40 | 0 to r.t. | 1.25 | 4.3 |

*In this reaction, AlBr$_3$ catalyst was added to a solution of adamantane in 1-hexene and n-hexane,, causing an exothermic reaction which boild off some 1-hexene and n-hexane.

TABLE 2

Comparison of Viscometric Properties and Thermal Stability of Total Alkyl Diamondoids

| Example Number | Sample | n* | Viscosity, c/S 100° C. | Viscosity, c/S 40° C. | VI | Pour Point °C. | Thermal Stability % KV 100 Change 300° C./ 24 hr | % KV 100 Change 288° C./ 72 hr | % Weight Loss 300° C./ 24 hr | % Weight Loss 288° C./ 72 hr |
| --- | --- | --- | --- | --- | --- | --- | --- | --- | --- | --- |
| 1 | hexyl adamantanes | 1.7 | 6.0 | 39.4 | 96 | −70 | −4.5 | −0.5 | 1.1 | 1.1 |
| 2 | hexyl adamantanes | 3.3 | 14.1 | 148.4 | 91 | −48 | +5.3 | +9.0 | 0.9 | 1.3 |
| 3 | octyl adamantanes | 3.0 | 9.5 | 73.0 | 108 | −60 | +2.8 | +5.3 | 1.0 | 09. |
| 4/5 | decyl adamantanes | >1.9 | 10.2 | 72.7 | 124 | −63 | +1.8 | +2.8 | 0.4 | 1.0 |
| 6 | Stock 509 | — | 5.6 | 29.5 | 131 | −68 | −12.9 | −25.0 | 1.9 | 2.6 |
| 7 | Stock 510 | — | 39.1 | 393.0 | 148 | −33 | −44.9 | −30.2 | 10.7 | 5.9 |

*Average number of alkyl substitution per diamondoid molecule

EXAMPLE 1

The crude product was 22.63 g yellowish oil. Unreacted adamantane, 2.68 g, was removed by Kügelrohr short-path distillation at a pot temperature of 100° C. and under about 10 in-Hg of vacuum. Raise the pot temperature to 250° C. to collect 16.00 g yellow oil as the product. GC, GC/MS, NMR study of the sample show that it is comprised of mono-, di-, tri-, and tetrahexyl adamantanes. Most of the substitutions on adamantane are by single hexyl groups, there are very little hexyl dimers or higher oligomers attached to adamantanes. Consequently, there are only a small amount of products having more than 34 carbons. NMR also showed that more than half of the hexyl groups are n-hexyl groups.

EXAMPLE 2

The crude product was 25.37 g yellowish oil, after removing unreacted hexene and solvent. Conversion of adamantane was complete. GC, GC/MS, and NMR of this product showed that the average degree of substitution was 3.3 hexyl groups/adamantane. Fragmentation patterns in MS proved that a majority of the alkyl groups on adamantane are hexyl. NMR indicated these are mostly n-hexyl, consistent with the lower reaction temperature compared with product from Example 1.

EXAMPLE 3

The crude product was 100.17 g yellowish oil. Conversion of adamantane was almost complete. GC showed it to be a mixture of mono-, di-, tri-, and tetra-octyl adamantanes. Most of them appeared to be n-octyl. A 76.75 g fraction of a yellowish oil collected between 75° and 206° C. pot temperature and 0.02 mm-Hg vacuum using Kügelrohr distillation was used for product testing. The average degree of substitution is 3.0 octyl groups per adamantane based on GC integration area alone, with a 4.0:20.0:41.3:33.9 ratio of mono-, di-, tri-, and tetra-octyl adamantanes.

EXAMPLE 4

The crude product was 46.94 g yellowish oil. Conversion of adamantane was almost complete. GC of this product showed that the average degree of substitution was >2.0 decyl groups per adamantane, because tetradecyl adamantanes were not eluted from this column. The GC indicated these were mostly n-decyl. The product of Example 4 was combined with product from Example 5 before testing.

EXAMPLE 5

The crude product was 48.46 g yellowish oil, after removing any unreacted adamantane and decene. GC of this product showed that the average degree of substitution was >2.5 decyl groups per adamantane, because tetra-decyl adamantanes were not eluted from this column. It was consistent with the higher ratio of decene/adamantane used. The GC indicated these were mostly n-decyl. It was combined with product from Example 4. Low-boiling products, 8.50 g, were removed at 100° C. (pot) and 0.05 mm-Hg using a Kügelrohr. A fraction of 76.64 g yellowish oil collected between 100° C. and 260° C. was tested for product properties. It had an average degree of substitution of >1.9 decyl groups/adamantane based on GC, because tetra-decyl adamantanes were not eluted from this column.

EXAMPLE 6

Example 6 was a first mixture of 1-decene oligomers which is commonly used as a commercial synthetic lube base stock.

EXAMPLE 7

Example 7 was a second mixture of 1-decene oligomers which is commonly used as a commercial synthetic lube base stock.

EXAMPLES 8–10

Examples 8–10 showed the effect of temperature and promoter on the reactions of adamantane with 1-decene using the AlBr$_3$ family of catalysts. The products of the reaction were analyzed. The analysis showed that the reaction gave higher conversion when CH$_2$Br$_2$ promoter was present. The effect of the temperature in the range examined was smaller and the differences may be due in part to normal variations. General procedure: To a 500 mL 2-neck round-bottom flask fitted with a pressure-equalized addition funnel and a condenser having a nitrogen bubbler were added 54.50 g adamantane and 100 mL n-hexane. In cases where the temperature of the reaction mixture was monitored, the flask was fitted with a pressure-equalized addition funnel having a nitrogen bubbler and a thermocouple. Catalyst, 3.0 mmoles of 1.0M AlBr$_3$/CH$_2$Br$_2$ solution or AlBr$_3$ solid, was added to the flask with stir. One mole of 1-decene was added slowly to the flask over a period of time. The reaction mixture was stirred for an additional period of time after all 1-decene had been added. Following usual aqueous work-up, the crude product was vacuum distilled using a Normag distilling apparatus to remove low-boiling material to give the crude lube range product.

temperature monitoring and/or control, and a stopper were added 54.50 g (0.40 mole) adamantane powder and 100 mL n-hexane. The catalyst was added. If the reaction was heated, catalyst was added after the reaction mixture had reached the pre-set temperature. Then 140.3 g (1.0 mole) of 1-decene was added from the funnel to the flask with magnetic stir over several hours. The reaction mixture was stirred for an additional period before being worked up using the usual aqueous wash process. Any unreacted starting materials were removed. The total alkylates were analyzed using GC. The details were summarized in Table 4. Table 5 compares the results of AlBr$_3$ and AlCl$_3$ catalyzed reaction of adamantane and 1-decene.

TABLE 4

| | | | | During olefin addn. | | After olefin addn. | | Crude Total Alkylate Product | |
| --- | --- | --- | --- | --- | --- | --- | --- | --- | --- |
| Example Number | AlCl$_3$ g | H$_2$O added | External Heating | Temp. °C. | hrs | Temp. °C. | hrs | % yield | mono-/di-/tri-/tetra-decyl Ad |
| 11 | 0.7 | None | No | 24–50 | 1.8 | r.t. | 17 | 35 | 49:30:16:5 |
| 12 | ~1.5 | None | Yes | 46–82 | 2.8 | 45 | 1.8 | 86 | 31:38:27:4 |
| 13 | 0.8 | None | Yes | 48–61 | 2.0 | 50 | 2.0 | 43 | 41:37:20:2 |
| 14 | 0.9 | None | Yes | 46–58 | 2.3 | 500 | 4.4 | 78 | 38:38:21:4 |
| 15 | 1.49 | None | Yes | 48–75 | 2.0 | 50 | 3.0 | 89 | 27:34:27:11 |
| 16 | 1.43 | 0.10 g | Yes | 48–63 | 2.7 | 50 | 3.5 | 80 | 47:38:14:1 |

*The lube yield is defined as wt. % of product vs. total wt. of diamondoids and 1-decene.
$^S$The product from this Example was examined quantitatively: conversion rates for adamantane and 1-decene were 94.3% and 99.7%, respectively. About 3.4% of 1-decene was converted to n-decane. About 2.7% of 1-decene was isomerized to other isomers. The bromine number for the total alkylate product was 5.4.
Determined by GC analysis based on area only using a 25 m × 0.32 mm × 0.25 mm WCOT fused silica gel column from Chrompack using a temperature program of 150° C. for 2 minutes-ramp to 300° C. at 5° C./minute-hold at 300° for 88 minutes, injector and detector at 310° C.

TABLE 5

Comparison of AlBr$_3$ and AlCl$_3$ catalyzed reaction of adamantane and 1-decene (1.0:2.5 molar ratio)

| Example | Catalyst | Conversion, % | | % other decenes | % n-decane | Total Alkylates | | | | |
| --- | --- | --- | --- | --- | --- | --- | --- | --- | --- | --- |
| | | 1-decene | Ad—H | | | % Yield | Br$_2$# | (decyl)$_n$Ad,n = 1, 2, 3, 4 | kv100, cS | VI |
| 8 | AlBr$_3$/CH$_2$Br$_2$ | 100 | 87 | 0.6 | 2.4 | 95 | 1.6 | 19:39:29:14 | 11.4 | 124 |
| 15 | AlCl$_3$ | 99.7 | 94 | 2.7 | 3.4 | 89 | 5.4 | 27:34:27:11 | 11.8 | 117 |

*The lube yield is defined as wt. % of product vs. total wt. of diamondoids and 1-decene.
Determined by GC analysis based on area only using a 25 m × 0.32 mm × 0.25 mm WCOT fused silica gel column from Chrompack using a temperature program of 150° C. for 2 minutes-ramp to 300° C. at 5° C./minute-hold at 300° C. for 88 minutes, injector and detector at 310° C.

EXAMPLES 17–19

Examples 17–19 show the separation of lube ranges products from the total alkylates from Examples 8–16. Tables 6 and 7 summarize the results. A comparison of the results between AlCl$_3$ and AlBr$_3$/CH$_2$Br$_2$ catalyzed reactions between adamantane and 1-decene shown in Table 7 revealed that the lube product from

TABLE 3

Reaction of adamantane with 1-decene (1.0:2.5 molar ratio) catalyzed by AlBr$_3$

| Example Number | % conversion | | Catalyst (3.0 mmoles) | During olefin addn. | | After olefin addn. | | Crude Lube Product | | | |
| --- | --- | --- | --- | --- | --- | --- | --- | --- | --- | --- | --- |
| | Ad—H | 1-decene | | Temp. °C. | hrs | Temp. °C. | hrs | b.p. ≧°C./mm-Hg | % yield* | % D—H$^S$ | Br$_2$# |
| 8 | 87 | 100 | AlBr$_3$/CH$_2$/Br$_2$ | 17–21 (bath) | 2.7 | r.t. | 20 | 120/0.50 | 95 | 25 | 1.6 |
| 9 | 79 | 85 | AlBr$_3$/CH$_2$/Br$_2$ | 22–51 | 3 | r.t. | 40 | 135/0.3 | 79 | 28 | — |
| 10 | 81 | 75 | AlBr$_3$ | 21–44 | 2 | r.t. | 85 | 125/0.25 | 63 | 30 | — |

*The lube yield is defined as wt. % of product vs. total wt. of adamantane and 1-decene.
$^S$This represents the wt. % of diamondoids in the lube products, estimated by mass balance and GC analysis.

EXAMPLES 11–16

Examples 11–16 examine the reaction of 1-decene and adamantane using AlCl$_3$ as the catalyst. General Procedure: To a 500 mL 4-necked round-bottom flask fitted with a reflux condenser having a nitrogen bubbler, a pressure-equalized addition funnel, a thermocouple for AlBr$_3$/CH$_2$Br$_2$ catalyzed reaction had higher VI and lower pour points. The difference in viscosity of these two products was at least in part due to different composition of these two: Example 17 had more mono-decyl adamantanes and less tetra-decyl adamantanes compared to Example 18.

EXAMPLE 17

The alkylate products from Examples 8-10 were combined and distilled for 8 hours using a Kügelrohr apparatus at a pot temperature of 150°-155° C. and under a vacuum of 0.2 mm-Hg. The trap was cooled in a dry-ice/acetone bath. Out of the initial 450 g product, 77.8 g was distilled and 372 g remained in the original flask. GC analysis showed that the former was an 1:81:18 mixture of decene dimers, mono-decyl adamantanes, and di-decyl adamantanes based on GC integration only. The latter was a 5:58:33:4 mixture of mono-, di-, tri-, and tetra-decyl adamantanes based on GC integration only. The high boiling lube product had a bromine number of 1.2. The crude lube range product was hydrogenated at 200° C. under ~500 psi of $H_2$ using ~1% (wt.) of $Ni/SiO_2$ catalyst to give the final lube product.

73% of the original starting materials' weight. The crude lube range product was hydrogenated at 200° C. under ~500 psi of $H_2$ using ~1% (wt.) of $Ni/SiO_2$ catalyst to give the final lube product.

EXAMPLE 19

The total alkylate products from Examples 11-14 and 16 were combined and distilled using a Kügelrohr at a pot temperature of 140° C. and a vacuum of 0.08 mm-Hg to remove most of the mono-decyl adamantanes and some di-decyl adamantanes. This fraction accounted for 26% of the original starting materials for the five reactions. GC analysis showed that the former was an 15:77:8 mixture of decene dimers, mono-decyl adamantanes, and di-decyl adamantanes based on GC integration only. The lube range products remained in the pot accounted for 38% of the combined starting materials' weight.

TABLE 6

| | Separation of lube products from reactions of adamantane with 1-decene catalyzed by $AlX_3$ | | | | | | | | |
|---|---|---|---|---|---|---|---|---|---|
| Ex. | Crude $C_{30}$ + Lube Products | | | | | Crude $C_{20}$ Products | | | |
| No. | yield$^S$ | kv 100, cS | VI | $Br_2$# | (Decyl)$_n$Ad, n = 1, 2, 3, 4 | yield$^S$ | kv 100° C., cS | VI | (Decyl)$_n$Ad, n = 1, 2* |
| 17 | ~80% | 12.08 | 122 | 1.2 | 5:58:33:4 | ~15% | 5.11 | 130 | 81:18 |
| 18 | 73% | 16.81 | 113 | 2.3 | 2:51:36:11 | 16% | 3.11 | 100 | 77:8 |
| 19 | 36% | 14.04 | 117 | 2.6 | 3:59:33:5 | 26% | 6.23 | 135 | 74:19 |

$^S$ The lube yield is defined as wt. % of product vs. total wt. of diamondoids and 1-decene.

Determined by GC analysis based on area only using a 25 m × 0.32 mm × 0.25 mm WCOT fused silica gel column from Chrompack using a temperature program of 150° C. for 2 minutes-ramp to 300° C. at 5° C./minute-hold at 300° C. for 88 minutes, injector and detector at 310° C.

*Determined by GC analysis based on area only using a 60 m × 0.32 mm × 1 mm SPB-1 column from Supelco, using a temperature program of 150° C. for 2 minutes-ramp to 300° C. at 50° C./minute-hold at 300° C. for 88 minutes, injector and detector at 310° C.

TABLE 7

| | Properties of hydrogenated lube products from reactions of adamantane with 1-decene catalyzed by $AlX_3$ | | | | | | | | |
|---|---|---|---|---|---|---|---|---|---|
| | Viscosity, cS | | | Pour Point | Bromine | Thermal Stability Tests under nitrogen | | | |
| | | | | | | % kv 100 Change | | % Weight Loss | |
| Example | 100° C. | 40° C. | VI | °C. | number | 300° C./24 hr | 288° C./72 hr | 300° C./24 hr | 288° C./72 hr |
| 17 | 12.03 | 92.24 | 124 | <−48.6 | 1.3 | −0.2 | −0.6 | 3.6 | 0.6 |
| 18 | 17.06 | 158.6 | 116 | −43.3 | 1.7 | −6.1 | −9.1 | 1.4 | 1.8 |

EXAMPLE 18

The total alkylate product from Example 15 was distilled using a Kügelrohr at a pot temperature of 160° C. and a vacuum of 0.20 mm-Hg for about 2.5 hours to remove most of the monodecyl adamantanes and some di-decyl adamantanes. This fraction accounted for 16% of the original starting materials for the reaction. GC analysis showed that the former was an 15:77:8 mixture of decene dimers, mono-decyl adamantanes, and di-decyl adamantanes based on GC integration only. The lube range products remained in the pot accounted for

EXAMPLES 20-23

Examples 20-23 examine the effect of reaction temperature, reactants ratio, promoters such as water, and nature of the olefin on the lube products for reactions of adamantane with alpha-olefins under $AlCl_3$ catalysis. Table 8 summarized these reactions and Table 9 the properties of the resulting hydrogenated lube products. The results showed that 1-tetradecene gave products with higher VI and pour point. The addition of water did promote the reaction somewhat and gave a lube with higher viscosity.

TABLE 8

| | Reaction of adamantane and alpha-olefin using $AlCl_3$ catalyst | | | | | | | | | | | | | |
|---|---|---|---|---|---|---|---|---|---|---|---|---|---|---|
| Example | Adamantane | | alpha-Olefin used | | | $AlCl_3$ | During olefin addn. | | After olefin addn. | | Crude Lube Product | | | |
| number | g | % conv. | Cpd | g | % conv. | g | Temp. °C. | hrs | Temp. °C. | hrs | g | % yield* | % D—H$^S$ | $Br_2$# |
| 20 | 40.87 | 87 | $C_{14}$ | 147.3 | 98 | 4.07 | 63–78 | 1.8 | 70–77 | 2.7 | 163 | 87 | 20 | 0.9 |
| 21 | 27.25 | 99 | $C_{10}$ | 98.2 | 99 | 1.91 | 50–59 | 2.5 | 48–52 | 4.0 | 148 | 92 | 23 | 1.2 |
| 22 | 102.2 | 98 | $C_{10}$ | 315.6 | 93 | 3.0 | 60–69 | 2.8 | 60–64 | 7.7 | 371 | 89 | 24 | 0.2 |
| 23 | 102.2 | 100 | $C_{10}$ | 315.6 | 92 | 3.0 | 60–67 | 2.6 | 60–64 | 78 | 366 | 88 | 25 | 1.1 |

*The lube yield is defined as wt. % of product vs. total wt. of diamondoids and alpha-olefin.

$^S$This represents the wt. % of diamondoids in the lube products, estimated by mass balance and GC analysis.

$^{30}$In this Example, 0.15 g water was added before $AlCl_3$ was added.

TABLE 9 uz,12/53 Properties of hydrofinished lube products from reaction of adamantane with alpha-olefins

| Example Number | Viscosity, cS 100° C. | Viscosity, cS 40° C. | VI | Pour Point °C. | Br$_2$# | Lube b.p. ≧ °C./mm-Hg* | Thermal Stability Tests under nitrogen % viscosity change, 100° C. 300° C./24 hr | % viscosity change, 100° C. 288° C./72 hr | % Weight Loss 300° C./24 hr | % Weight Loss 288° C./72 hr |
|---|---|---|---|---|---|---|---|---|---|---|
| 20 | 17.47 | 138.0 | 139 | −11.4 | 0.1 | 125/1.04 | −0.1 | +11.5 | 2.8 | 9.1 |
| 21 | 14.69 | 121.7 | 123 | <−46.3 | 1.0 | 155/0.74 |  | −8.5 |  | 1.2 |
| 22 | 21.23 | 215.7 | 117 | −41.6 | 0.7 | 183/0.69 |  | 8.1 |  | 2.0 |
| 23 | 26.78 | 306.6 | 115 | −39.6 | 0.4 | 185/0.63 |  | 11.8 |  | 5.9 |

*Before hydrogenation, crude products were distilled to remove unreacted starting material and low-boiling products using a Kügelrohr (Example 20), a Normag (Examples 21 and 23), or a 12" Vigreux column and a Normag distilling apparatus (Example 22) up to the boiling points (or pot temperatures) specified in the table.

EXAMPLES 24–27

Examples 24–27 illustrate the results from reaction of pure diamantane and alpha-olefin such as 1-decene with AlCl$_3$ catalyst.

General Procedure: To a 500 mL 4-necked round-bottom flask fitted with a reflux condenser having a nitrogen bubbler, a pressure-equalized addition funnel, a thermocouple for temperature monitoring and/or control, and a stopper were added diamantane powder and 75 mL n-heptane (Example 24) or 45 mL n-hexane (Example 25–27). The catalyst was added after the reaction mixture had reached the pre-set temperature. Then 1-decene was added from the funnel to the flask with magnetic stir over several hours. The reaction mixture was stirred for an additional period before being worked up using the usual aqueous wash process. Any unreacted starting materials were removed. The details were summarized in Table 10 and 11.

TABLE 10

Reactions of pure diamantane with 1-decene using AlCl$_3$ as the catalyst.

| Example number | Diamantane g | Diamantane % conv. | 1-decene g | 1-decene % conv. | D—H/decene mole ratio | AlCl$_3$ g | During olefin addn. Temp. °C. | During olefin addn. hrs | After olefin addn. Temp. °C. | After olefin addn. hrs | Crude Lube Product g | Crude Lube Product % yield* | Crude Lube Product % D—H$^S$ | Br$_2$# |
|---|---|---|---|---|---|---|---|---|---|---|---|---|---|---|
| 24 | 47.1 | 98 | 105.2 | 93 | 1.0:2.5 | 2.0 | 60–75 | 2 | 60–62 | 3.0 | 138 | 91 | 33 | 2.2 |
| 25 | 28.25 | 99 | 94.68 | 99 | 1.0:4.5 | 2.0 | 48–54 | 2.0 | 45–52 | 4.5 | 119 | 97 | 22 | 3.5 |
| 26 | 28.25 | 99 | 94.68 | 99 | 1.0:4.5 | 1.9 | 70–83 | 1.8 | 75–82 | 4.4 | 112 | 91 | 23 | 3.1 |
| 27 | 28.31 | ~99 | 126.4 | ~99 | 1.0:6.0 | 2.3 | 59–67 | 1.2 | 57–63 | 12 | 146 | 94 | 18 | 4.0 |

The solvent used in this Example was n-heptane.
*The lube yield is defined as wt. % of product vs. total wt. of diamondoids and 1-decene.
$^S$This represents the wt. % of diamondoids in the lube products, estimated by mass balance and GC analysis.

TABLE 11

The properties of hydrofinished lube products from reactions of diamantane and 1-decene under AlCl$_3$ catalysis

| Example Number | Viscosity, cS 100° C. | Viscosity, cS 40° C. | VI | Pour Point °C. | Br$_2$# | Lube b.p. ≧ °C./mm-Hg* | Thermal stability under nitrogen % viscosity change 100° C. 300° C./24 hr | % viscosity change 100° C. 288° C./72 hr | % Weight Loss 300° C./24 hr | % Weight Loss 288° C./72 hr |
|---|---|---|---|---|---|---|---|---|---|---|
| 24 | 20.23 | 219.5 | 107 | −38.1 | 0.0 | 142/0.40 | −2.2 | −4.2 | 2.5 | 1.4 |
| 25 | 26.58 | 297.0 | 118 | −39.1 | 0.6 | 120/0.63 |  | −2.9 |  | 5.6 |
| 26 | 24.60 | 266.4 | 117 | −40.6 | 0.8 | 168/0.83 |  | −11.0 |  | 1.7 |
| 27 | 28.26 | 297.4 | 128 | −39.0 | 1.5 | 163/0.4 |  | −17.8 |  | 3.1 |

*Before hydrogenation, crude products were distilled to remove unreacted starting material and low-boiling products using a Kügelrohr (Example 24), a Normag (Examples 25 and 27), or a 12"Vigreux column and a Normag distilling apparatus (Example 26) up to the boiling points (or pot temperatures) specified in the table.

EXAMPLES 28–30

Examples 28–30 illustrate the reactions of adamantane with other olefins. The reactions were carried out in much the same way as in examples above using AlCl$_3$ as the catalyst. The results were summarized in Tables 12 and 13.

TABLE 12

The reactions of adamantane with other olefins using AlCl$_3$ as the catalyst

| Ex. # | Adamantane g | Adamantane % conv. | Olefin used Compound | Olefin used g | Olefin used % conv. | AlCl$_3$ g | During olefin addn. Temp. °C. | During olefin addn. hrs | After olefin addn. Temp. °C. | After olefin addn. hrs | Crude Lube-range or Total Alkylates % yield* | Crude Lube-range or Total Alkylates % D—H$^S$ | Br$_2$# |
|---|---|---|---|---|---|---|---|---|---|---|---|---|---|
| 28 | 27.25 | 66 | C$_{20}$ vinylidene | 112.2 | 68 | 3.0 | 59–67 | 1.8 | 60–61 | 12 | 53 | 22 | 6.8 |
| 29 | 20.44 | 87 | neo-hexene | 70.1 | 32 | 3.0 | 54–76 | 2.5 | ~60 | 2.3 | 43 | 46 | — |
| 30 | 20.44 | 89 | diMe-2-butene | 70.1 | 41 | 1.2 | r.t. ~50 | 2.0 | ~70 | 50 | 39 | 51 | — |

*The lube yield is defined as wt. % of product vs. total wt. of diamondoids and 1-decene.
$^S$This represents the wt. % of diamondoids in the lube products, estimated by mass balance and GC analysis.
Obtained from Gulf Research and Development Co. Our NMR analyses of this "C$_{20}$ vinylidene" showed that it was a mixture of at least five olefins with about half C$_{20}$ vinylidene.

TABLE 13

| | Properties of the hydrofinished lube product from adamantane and C$_{20}$ vinylidene | | | | | | | |
|---|---|---|---|---|---|---|---|---|
| Example number | Viscosity, cS | | | Pour Point °C. | Br$_2$# | Lube b.p. ≧ °C./mm-Hg | Thermal stability 288° C./72 hr/N$_2$ | |
| | 100° C. | 40° C. | VI | | | | % kv 100 Change | % Weight Loss |
| 28 | 7.44 | 45.11 | 130 | −15.7 | ~ | ~135/0.22 | +4.4 | 3.1 |

*Before hydrogenation, the crude product was distilled to remove unreacted starting material and low-boiling products using a 12" Vigreux column and a Normag distilling apparatus up to the boiling points specified in the table.

Oxidative Stability of the Products

Oxidative stability of the products were assessed using two methods after blending the hydrocarbon lube in a commercial package containing anti-oxidants and other components. One method used was induction period (IP) method by high pressure DSC. In this method, a few mg of the sample was place in an open Al pan in the DSC. The apparatus was filled with oxygen to 500 psi. The temperature of the sample was increased from 40° to 185° C. at 50° C./min and was held at 185° C. for an additional 80 min. The induction period was defined as the time required to reach ~10% of the eventual exotherm peak height for each sample. The reported numbers include averages of several runs. The samples were also tested for oxidative stability at 325° F. for 72 or 144 hours. The results are shown in the table below. Most indications from both methods showed that our new lube compositions showed better oxidative stability than the conventional PAO type lubricants.

lyst selected from the group consisting of AlX$_3$ and BX$_3$ wherein X is a halogen, in the absence of added proton-donating catalyst promoter.

2. The method of claim 1 wherein said halogen is selected from the group consisting of chlorine, fluorine, and bromine.

3. The method of claim 1 wherein the molar ratio of α-olefin to diamondoid compound is from about 20:1 to about 1:1.

4. The method of claim 3 wherein the molar ratio of α-olefin to diamondoid compound is from about 2:1 to about 1:1.

5. The method of claim 1 wherein said α-olefin comprises 1-decene.

6. The method of claim 1 further comprising converting at least 80 weight percent of said α-olefin.

7. The method of claim 6 further comprising converting at least 90 weight percent of said α-olefin.

8. The method of claim 7 further comprising converting at least 95 weight percent of said α-olefin.

| | | Oxidative stability of diamondoid-modified PAO by B-10 and DSC IP | | | | | | | |
|---|---|---|---|---|---|---|---|---|---|
| | | Oxidative Stability Test Results at 325° F./72 hrs | | | | Oxidative Stability Test results at 325° F./144 hrs | | | |
| Example | DSC IP min | Sludge | kv 100% change | acid # mg KOH | % Pb loss | Sludge | kv 100% change | acid # mg KOH | % Pb loss |
| 3 | — | — | — | — | — | light | 15 | 0.34 | 4.65 |
| 18 | 60.2 | moderate | 3.79 | 0.08 | 0.78 | moderate | 162 | 10.63 | 1.39 |
| 20 | 63.9 | moderate | 3.62 | 0.07 | 0.55 | moderate | 7 | 0.20 | 0.59 |
| 24 | 50.5 | light | 3.44 | 0.10 | 0.44 | moderate | 130 | 7.57 | 1.12 |
| 6 | 49.4 | light | 3.09 | <0.05 | 0.81 | moderate, Nil | 57, 28 | 11.22, 5.27 | 1.67, 0.08 |
| 7 | 48.1 | light | 9.54 | 0.25 | 2.27 | moderate | 471 | 1.99 | 7.01 |

Changes and modifications in the specifically described embodiments can be carried out without departing from the scope of the invention which is intended to be limited only by the scope of the appended claims.

What is claimed is:

1. A method for selectively alkylating a diamondoid compound comprising reacting at least one α-olefin containing at least six carbon atoms with at least one diamondoid compound in the presence of an acid cata- 9. The method of claim 6 wherein less than 20 weight percent of said converted α-olefin forms oligomerate.

10. The method of claim 7 wherein less than 20 weight percent of said converted α-olefin forms oligomerate.

11. The method of claim 8 wherein less than 20 weight percent of said converted α-olefin forms oligomerate.

* * * * *